(12) United States Patent
Dobbins et al.

(10) Patent No.: US 11,679,170 B2
(45) Date of Patent: Jun. 20, 2023

(54) PAYMENT SANITIZING SYSTEM FOR POINT OF SALE

(71) Applicant: Ellenby Technologies, Inc., Woodbury Heights, NJ (US)

(72) Inventors: Aaron H. Dobbins, Cherry Hill, NJ (US); Bob M. Dobbins, Villanova, PA (US); Thomas Carullo, Marlton, NJ (US)

(73) Assignee: Ellenby Technologies, Inc., Woodbury Heights, NJ (US)

( * ) Notice: Subject to any disclaimer, the term of this patent is extended or adjusted under 35 U.S.C. 154(b) by 241 days.

(21) Appl. No.: 17/228,862

(22) Filed: Apr. 13, 2021

(65) Prior Publication Data

US 2021/0330832 A1    Oct. 28, 2021

Related U.S. Application Data

(60) Provisional application No. 63/013,663, filed on Apr. 22, 2020.

(51) Int. Cl.
| | |
|---|---|
| *A61L 2/10* | (2006.01) |
| *A61L 2/24* | (2006.01) |
| *A61L 2/26* | (2006.01) |

(52) U.S. Cl.
CPC ............ *A61L 2/10* (2013.01); *A61L 2/24* (2013.01); *A61L 2/26* (2013.01); *A61L 2202/11* (2013.01); *A61L 2202/14* (2013.01)

(58) Field of Classification Search
CPC ..... A61L 2/10; A61L 2/24; A61L 2/26; A61L 2202/11; A61L 2202/14
See application file for complete search history.

(56) References Cited

U.S. PATENT DOCUMENTS

| | | | | |
|---|---|---|---|---|
| 4,420,153 | A | * | 12/1983 | Winkler ................. G07D 11/50 271/304 |
| 5,374,814 | A | | 12/1994 | Kako et al. |
| 6,811,748 | B2 | | 11/2004 | Ettlinger et al. |

(Continued)

FOREIGN PATENT DOCUMENTS

WO    2013068973 A2    5/2013

OTHER PUBLICATIONS

"https://www.hitachi-omron-ts.com/news/202009-001.html.", Sep. 17, 2020.

(Continued)

*Primary Examiner* — Sean M Luck
(74) *Attorney, Agent, or Firm* — Ryan, Mason & Lewis, LLP

(57) ABSTRACT

A sanitizer is described which frames a payment media, such as a bill, a coin and a credit card, in an irradiation zone between narrowly spaced support walls having associated ultraviolet lamps arranged to irradiate the payment media for at least a predetermined minimum time period. In one approach a motorized transport transports the payment media to an entry point from which it falls into the irradiation zone. In another aspect, a gravity feed approach is employed to return the irradiated media item to a dispense zone. One application is to alleviate concern at a point of sale where customers and merchants are concerned about whether payment media may be carrying a dangerous virus.

20 Claims, 16 Drawing Sheets

(56) References Cited

U.S. PATENT DOCUMENTS

| | | | |
|---|---|---|---|
| 7,032,467 B2* | 4/2006 | Yoon | G01N 1/2202 |
| | | | 73/31.03 |
| 7,213,603 B2 | 5/2007 | Pinsky | |
| 7,778,456 B2* | 8/2010 | Jones | G07D 7/12 |
| | | | 705/43 |
| 7,975,908 B1* | 7/2011 | Greco | G07F 19/201 |
| | | | 235/379 |
| 9,415,124 B2 | 8/2016 | Baek | |
| 9,498,551 B2 | 11/2016 | Yanke | |
| 2003/0124039 A1 | 7/2003 | Ryan | |
| 2005/0053183 A1* | 3/2005 | Abe | G07D 7/121 |
| | | | 377/94 |
| 2005/0183928 A1* | 8/2005 | Jones | G07D 11/16 |
| | | | 194/207 |
| 2011/0253563 A1 | 10/2011 | Goldman | |
| 2013/0127506 A1 | 5/2013 | Kwak | |

OTHER PUBLICATIONS

"IES Committee Report: Germicidal Ultraviolet (GUV) Frequently Asked Questions", "IES Photobiology Committee", Apr. 15, 2020, Page(s) ISBN 978-0-87995-389-8, Publisher: Iluminating Engineering Society.

Publika, S., "https://en.publika.md/romanian-inventor-created-money-sterilizer-apparatus-2642146 foto4391913. html#gallery", Nov. 15, 2017.

* cited by examiner

PAYMENT SANITIZING SYSTEM FOR POINT OF SALE

CROSS-REFERENCE TO RELATED APPLICATION

The present application claims the benefit under 35 USC § 119 of U.S. Provisional Patent Application Ser. No. 63/013,663 filed Apr. 22, 2020 entitled Payment Sanitizing System which is assigned to the assignee of the present application and incorporated by reference herein in its entirety.

FIELD OF INVENTION

The present disclosure relates generally to improved methods and apparatuses for handling payment media, and more particularly addressing concerns about viruses and the like that might be carried by currency, coins, and credit cards when such media are utilized and change hands, for example, at a point of sale (POS).

BACKGROUND OF THE INVENTION

The current coronavirus pandemic has heightened concerns about the exchange of payment media possibly resulting in viral infection. In particular, paper currency and coins may come into contact with many hands. Credit cards also may raise similar users' concerns. A cashier receiving currency, coins or a credit card from a customer does not know the customer's health history and similarly, the customer does not know the cashier's health history. The same is true in a number of different contexts, such as when one receives cash from an automated teller machine (ATM).

A wide variety of patents and publications address such issues, such as U.S. Pat. No. 9,498,551B2 which addresses an anti-microbial cash drawer. In this context, this patent teaches inclusion of an ultraviolet C (UVC) light source inside a cash drawer to irradiate coins and notes with radiation with wavelengths between 200 and 290 nanometers (nm). Two 5 W 5 mm×240 mm long germicidal lamps are taught as preferred with each outputting 2600 microwatts/cm$^2$ at 1 inch distance operating at 900 Vrms and starting at 1500 Vrms to enable a quick start of operation at near full power. This patent does not appear to address how UVC penetrates down through a stack of stored notes or coins that are covered by other coins.

U.S. Pat. No. 7,213,603B2 addresses a system and method for toothbrush sanitation and storage. It teaches three minute timed exposure intervals periodically applied throughout the night with a germicidal bulb.

U.S. Published Patent Application No. 2011/0253563A1 addresses a currency sterilization apparatus employing a tray of UV bulbs that sits above a cash till for disinfecting currency comprising cash and coins. The UV bulbs are complemented by a disinfectant spray system also included in the tray.

U.S. Pat. No. 5,374,814A addresses a cash transaction machine and method with money disinfection which uses a heated roller (220° or 240° C.) and UV irradiation or a disinfecting liquid to clean bills and then to store them in a storage unit until later dispensed out a discharge port. Disinfecting of the bills occurs while they are being transported. Disinfection during transport includes application of several phases of UV exposure, heat application, liquid disinfecting spray, and ozone.

WO 2013/068973 A2 addresses apparatus for the disinfection, sterilization and cleaning of banknotes using a hinged UV lamp assembly including multiple UV lamps and a brush at the inlet. Notes sit on a motorized bill path. There is an optical bill sensor to detect a note entering the bill path. The note takes between 1 and 1.5 seconds to transport across the bill path with 1.2 seconds taught as being preferable.

U.S. Published Patent Application No. 2013/0127506A1 addresses decontaminating a mailbox by employing UVC lighting inside the mailbox along with ozone generators.

U.S. Published Patent Application No. 2003/0124039A1 addresses a system for sanitizing incoming mail using UVC or a comparable sanitizing mechanism in-line with the mail transport belt after letters are arranged so they are presented singularly during processing.

https://en.publika.md/romanian-inventor-created-money-sterilizer-apparatus-2642146 foto4391913.html#gallery describes a money sterilizing apparatus in which UV and ozone are used to clean cash and coins within 35 seconds with up to 50 notes processed at a time.

Hitachi-Omron Terminal Solutions Corporation introduced a currency disinfector system to disinfect banknotes using UVC light at speeds up to 1000 notes per minute by feeding the notes across a long, motorized pathway of UVC bulbs https://www.hitachi-omron-ts.com/news/202009-001.html.

U.S. Pat. No. 9,415,124B2 describes a bill sterilizer equipped with a counting machine using plasma ion sterilizers. This approach uses plasma generated clusters of ions to bombard clusters of bills over the course of a 30 second exposure.

U.S. Pat. No. 6,811,748B2 addresses a system for and method of sterilization of objects wherein objects are enclosed in a box with UVC light exposure.

IES Committee Report: Germicidal Ultraviolet (GUV)—Frequently Asked Questions, IES CR-2-20-V1 prepared by the IES Photobiology Committee ISBN 978-0-87995-389-8 ©2020 (Apr. 15, 2020) provides a wealth of information about germicidal UV and is incorporated by reference herein in its entirety.

SUMMARY OF INVENTION

While the above items address a wide variety of approaches, they do not, in a practical and effective manner, address the unique concerns presented during payment exchange at a POS as occurs at checkout at any store, for example. At the payment exchange, a customer presents a payment media, such as currency and coins or a credit card. The cashier takes the payment media and often returns change and a receipt. These exchanges must occur as quickly and as simply as possible to achieve a maximum level of profitability.

To attempt to address such needs, as well as, to address further POS and cash exchange concerns, the present invention according to one or more aspects provides a low cost UVC sanitizing system that avoids use of any motor drive elements in a sanitizing zone of the sanitizer to provide a low cost UVC payment media sanitizing system. Substantially no UVC light escapes the enclosure. The UVC system may suitably use mercury (Hg) germicidal lamps preferably T5G6 variety, or UVC LEDs.

The sanitizing system may be coupled with a note transporting motor drive system that may be part of a banknote validator motor drive. A banknote validator advantageously detects validity of the note, denomination of the note, and ensures the note is substantially flat and without folds when sanitized. Four T5G6 lamps distributed two each on both sides of broad surfaces of the bills, card, or coin may suitably be used to produce a total of about 6 W of UVC power.

A low cost UVC bill sanitizing system with a motor driven bill transport portion and display portion is advantageously provided according to one aspect of the present invention.

The display portion may indicate to a customer the value of the note. The display may also indicate if a note is present and ready to collect from the collection area.

A low cost bill sanitizing system is provided that is designed for table-top installation at a point of sale in a retail environment in which substantially all harmful levels of UVC radiation are shielded from users. Another suitable location is near an ATM.

A liquid sanitizer pump assembly is also advantageous for more general-purpose sanitation during payment transactions.

Cards and coins may be supported by a moveable platform to keep them in an optimal position for UVC decontamination for about two seconds before being released.

In one embodiment of the invention, a payment media sanitizing apparatus comprises a thin payment media directing mechanism that directs thin payment media from an insertion point to a sanitization zone internal to the payment sanitizing apparatus. The sanitization zone has a length slightly longer than a longest thin payment media to be sanitized by the payment media sanitizing apparatus and comprising a thin payment media support and associated ultraviolet sources to irradiate the thin payment media when it is in the sanitization zone. The apparatus also comprises a release mechanism comprising a moveable support member in a first position supporting a leading edge of the thin payment media when the thin payment media is in the sanitization zone during sanitizing and in a second position allowing return of the thin payment media and a mechanical release lever operated to move the moveable support member and return the thin payment media to a return retrieval tray.

A more complete understanding of the present invention, as well as, further features and advantages of the invention will be apparent from the following discussion and the drawings.

DETAILED DESCRIPTION

Figure 1:
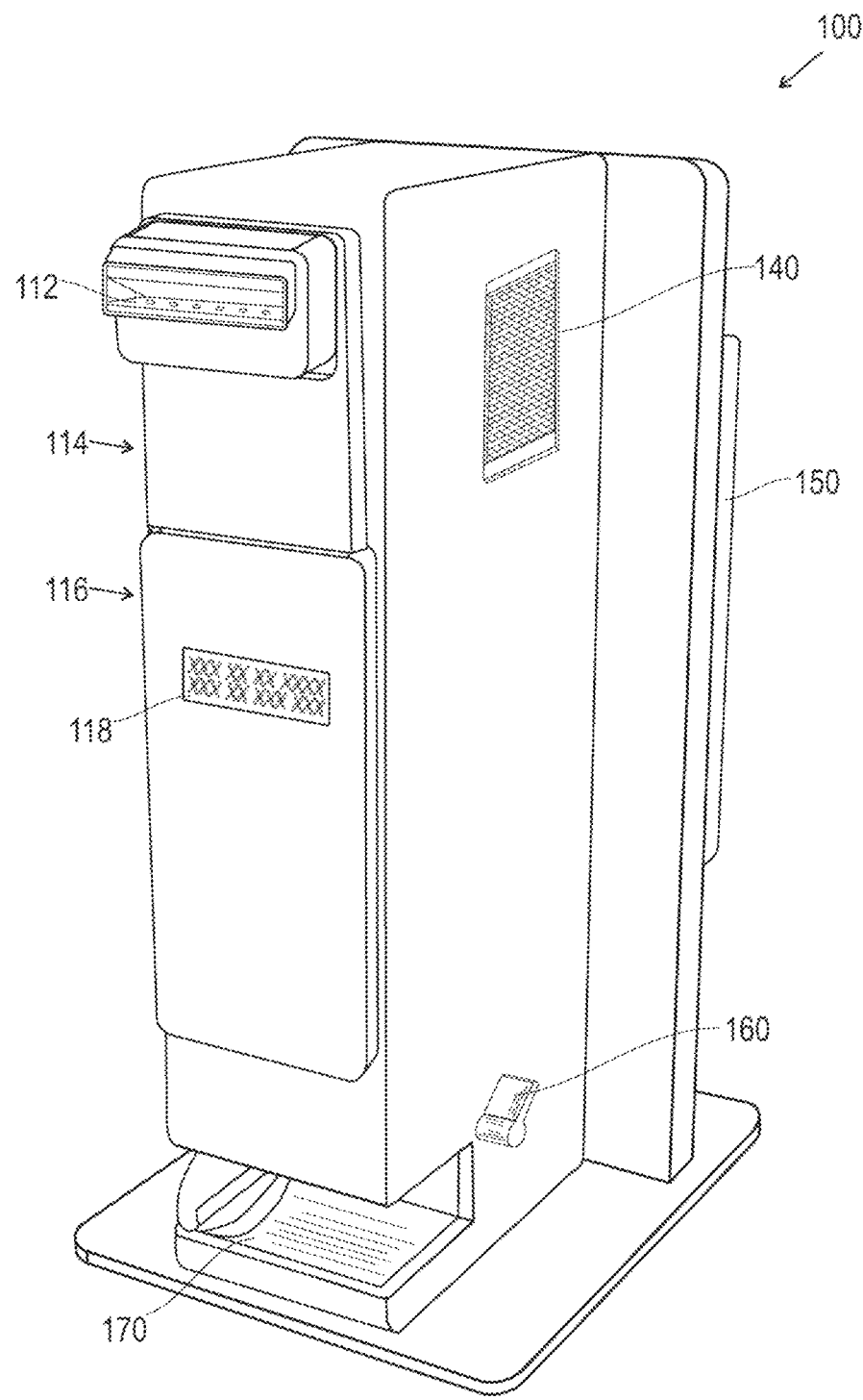
FIG. 1 shows a front perspective view of one embodiment of a payment sanitizer system for point of sale (POS) in accordance with the present invention.

FIG. 1 shows a payment sanitizer system 100 in accordance with an embodiment of the present invention adapted to a point of sale or other table top environment, such as, a small table beside an ATM. The payment sanitizer system 100 substantially reduces viruses on paper currency, credit cards, and coins. It will be recognized that in addition to currency, checks and other paper items such as coupons of appropriate size and shape can also be sanitized. In a presently preferred embodiment, the payment sanitizing system, will validate currency utilizing a bill validator 110 (seen in FIG. 3) having a bill insert slot 112. In the presently preferred embodiment, the payment sanitizing system 100 has overall dimensions of approximately 17" tall, 8" wide and 10" deep or smaller so as to not take up too much of the valuable real estate at the POS.

The bill validator 110 receives an inserted piece of currency, such as a U.S. $10 bill through the bill insert slot 112. A motorized bill transport 114 internal to the payment sanitizing system 100 transports the $10 bill past the validation sensors of the bill validator 110 and if determined to be valid by control electronics 116 (internal) drives the $10 bill to a release point at which the motorized bill transport no longer controls the movement of the bill. While a motorized bill transport which is part of a bill validator is presently preferred, if it is desired to reduce the overall cost of the unit a motorized bill transport without any additional functionality may suitably be employed.

The transport of the bill validator may be programmed to match or exceed the time needed to irradiate a bill in the irradiation zone. Thus, if there are multiple bills to be sanitized, a first can go to the irradiation zone to be cleaned and removed as a next item is inserted into the bill validator where it is held until the first is removed.

A display 118 can display the amount of the bill, $10, and when the sanitizing process is completed, for example. If the customer is proffering coins or a credit card, a manual drop chute 140 is used to insert them. A hand sanitizer module 150 (better seen in FIG. 2C) is provided so either the customer or the merchant can sanitize his or her hands before taking the sanitized bill, coins or card. To remove the sanitized item, a payment release mechanism or lever 160 is operated allowing the item to fall under the influence of gravity to a payment retrieval tray 170.

In a presently preferred embodiment, surfaces frequently touched by customers or merchants, such as lever 160 or dispense tray 170 may be brass, bronze or copper which cause an oxidation-reduction reaction with viruses and bacteria, see, for example, https://www.smithsonianmag.com/science-nature/copper-virus-kill-180974655/, detrimental to any virus occurring on their surfaces.

Figure 2C:
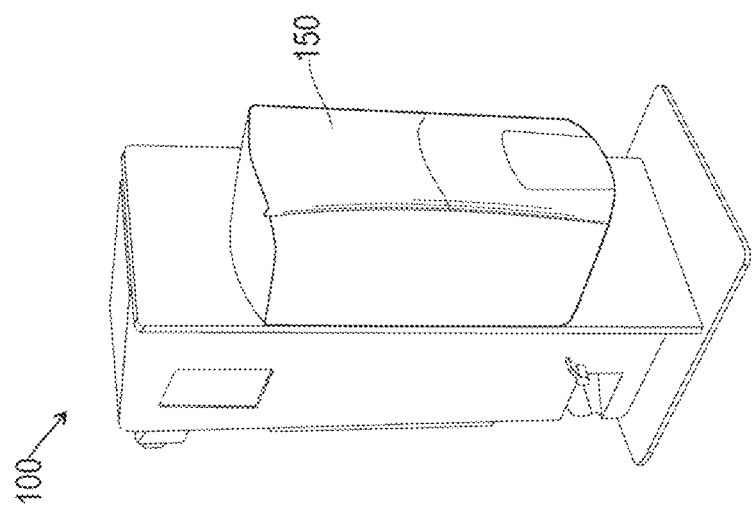
FIGS. 2A-2C show a series of views of the payment sanitizer system of FIG. 1 collectively providing a 360° view thereof.
Figure 2B:
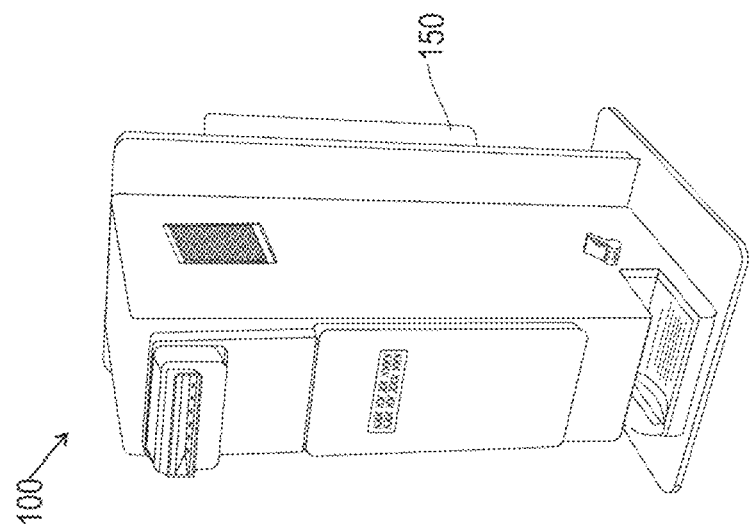
Figure 2A:
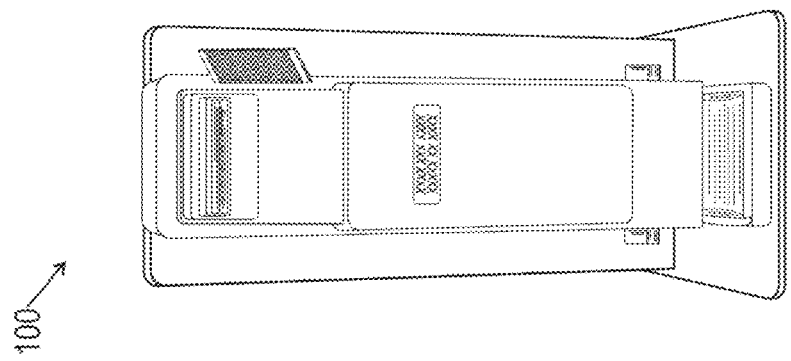

FIGS. 2A-2C show rotated perspective views of the sanitizer system 100.

Figure 3:
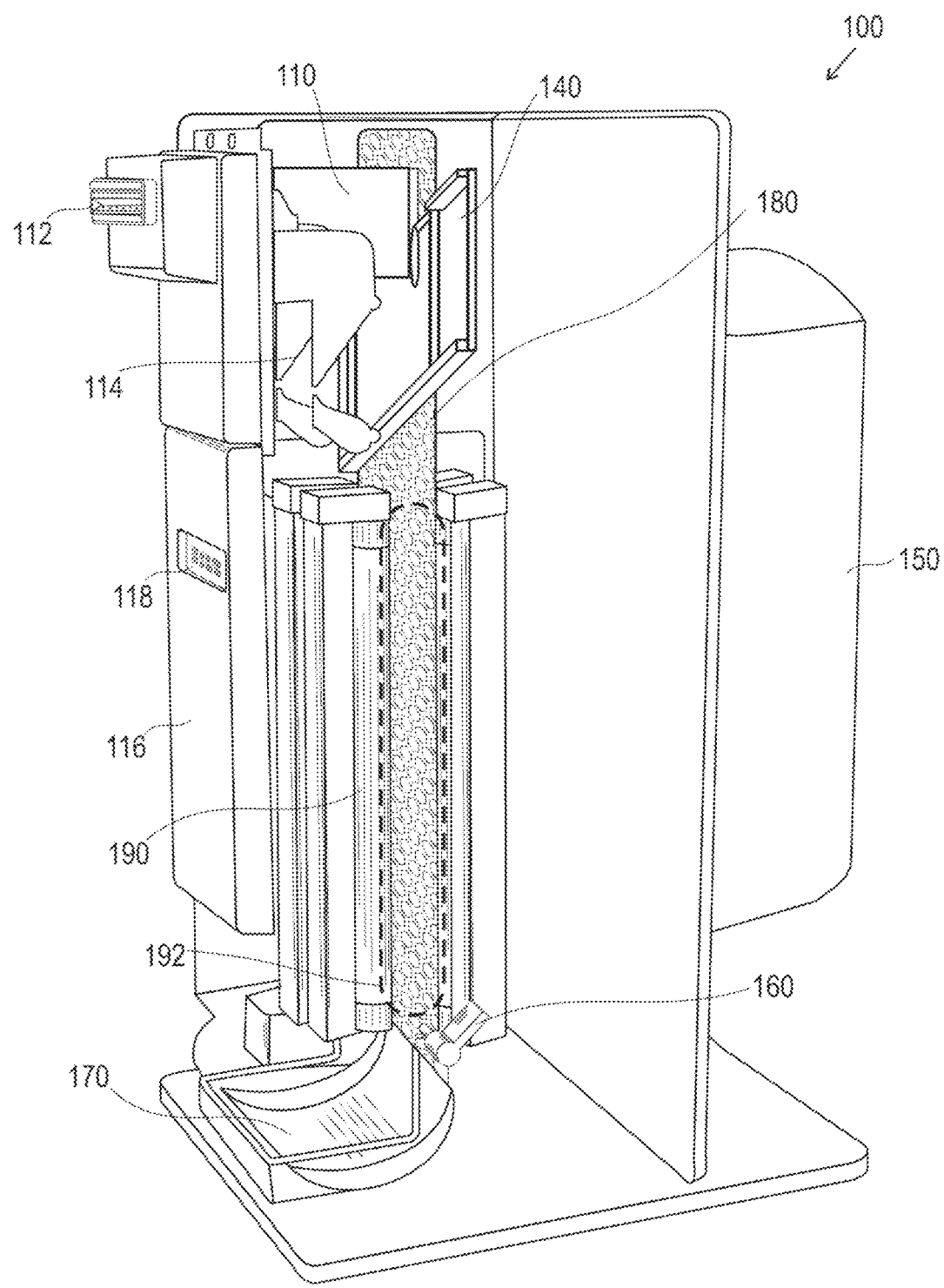
FIG. 3 shows a cutaway right side perspective view of the payment sanitizer system of FIG. 1 illustrating internal features thereof.
Figure 4B:
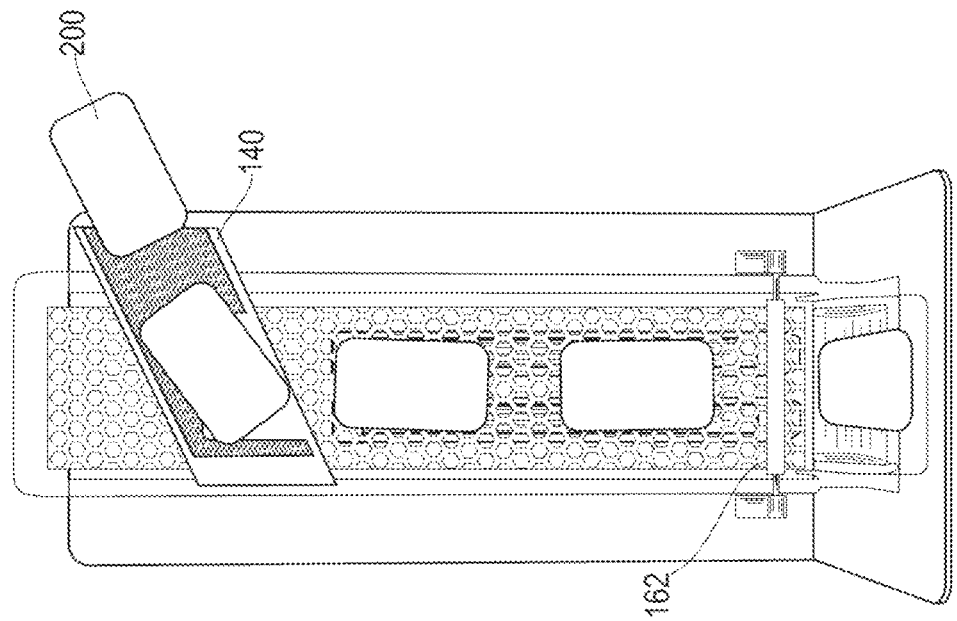
FIGS. 4A and 4B show a side view cutaway and a front view cutaway, respectively, to illustrate aspects of bill or note travel and card and coin travel, respectively.
Figure 4A:
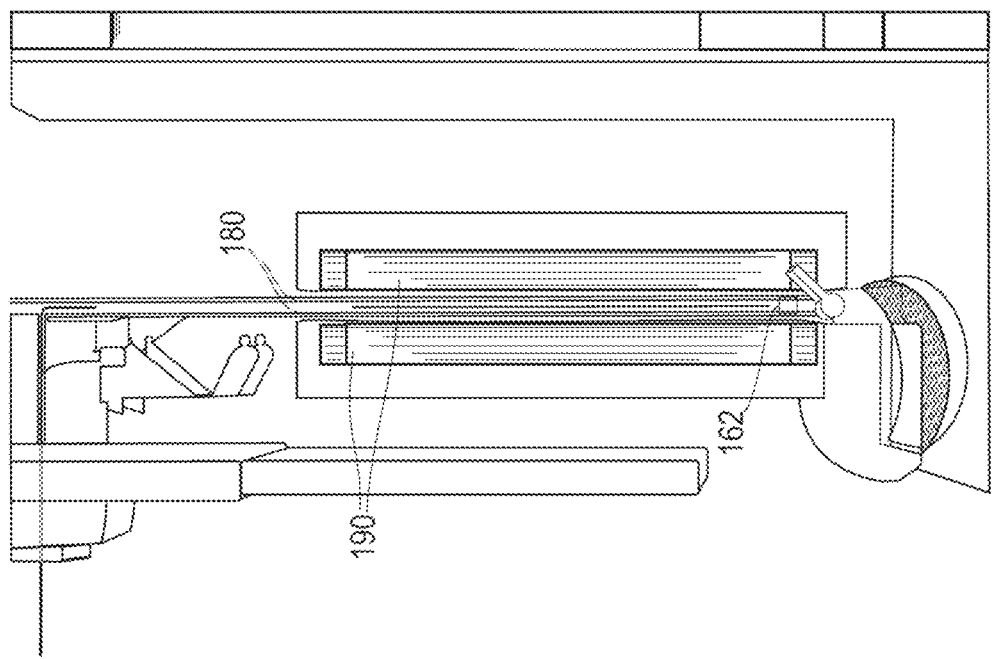

FIGS. 3 and 4A illustrate a payment media path to achieve sanitation in accordance with the present invention. As addressed above, a note is presented to the front of the note transporter 114 by inserting an edge into the bill insert slot 112. The motor drive of transporter 114 transports and flattens the note and sensors ensure the bill is not folded at a corner or otherwise. The note is directed towards an irradiation zone in which UVC lamps (four lamps preferably two on either side) collectively 190 irradiate the note. When the sanitizer apparatus 100 is in relatively steady usage, the UVC lamps are preferably left on and only powered down after a predetermined period of inactivity.

Perforated aluminum sheets (one on either side) collectively 180 frame and support the note. A bottom or lead edge of the note rests on a moveable support member 162 in a first position (FIG. 4A) until sanitizing is complete and a release mechanism or lever 160 is operated to move the moveable support member 162 to a second position out of the way. The note then falls under the influence of gravity or is otherwise transported to a payment retrieval return or dispenser tray 170.

Referring to FIGS. 3 and 4B, a media path for a credit card 200 (shown in FIG. 4B) or a coin (not shown) is described. A card 200 or coin is inserted into a manual entry slot 140 along a ramp and drops down between the aluminum side plates 180 until its lead edge rests on top of the moveable support member 162 where it is irradiated by the UVC lamps 190. Upon completion of irradiation, a display 118 indicates the irradiation is complete and the release lever 160 is actuated to move the moveable support member so that the card 200 or a coin or coins can fall to the dispense tray 170. The display may also be used to remind the customer or merchant to use the hand sanitizer prior to picking up the cleaned payment media.

In an alternate embodiment of the design, coins may also pass through a singulating unit such as a bulk coin acceptor with a rotary wheel, for example, the Crane Payment V² Pelicano™. This approach would allow for bulk input of a handful of coins into the side of the payment sanitizer system 100 and one at a time passage of the coins through irradiation zone 192 between the UVC lamps 190.

Figure 5:
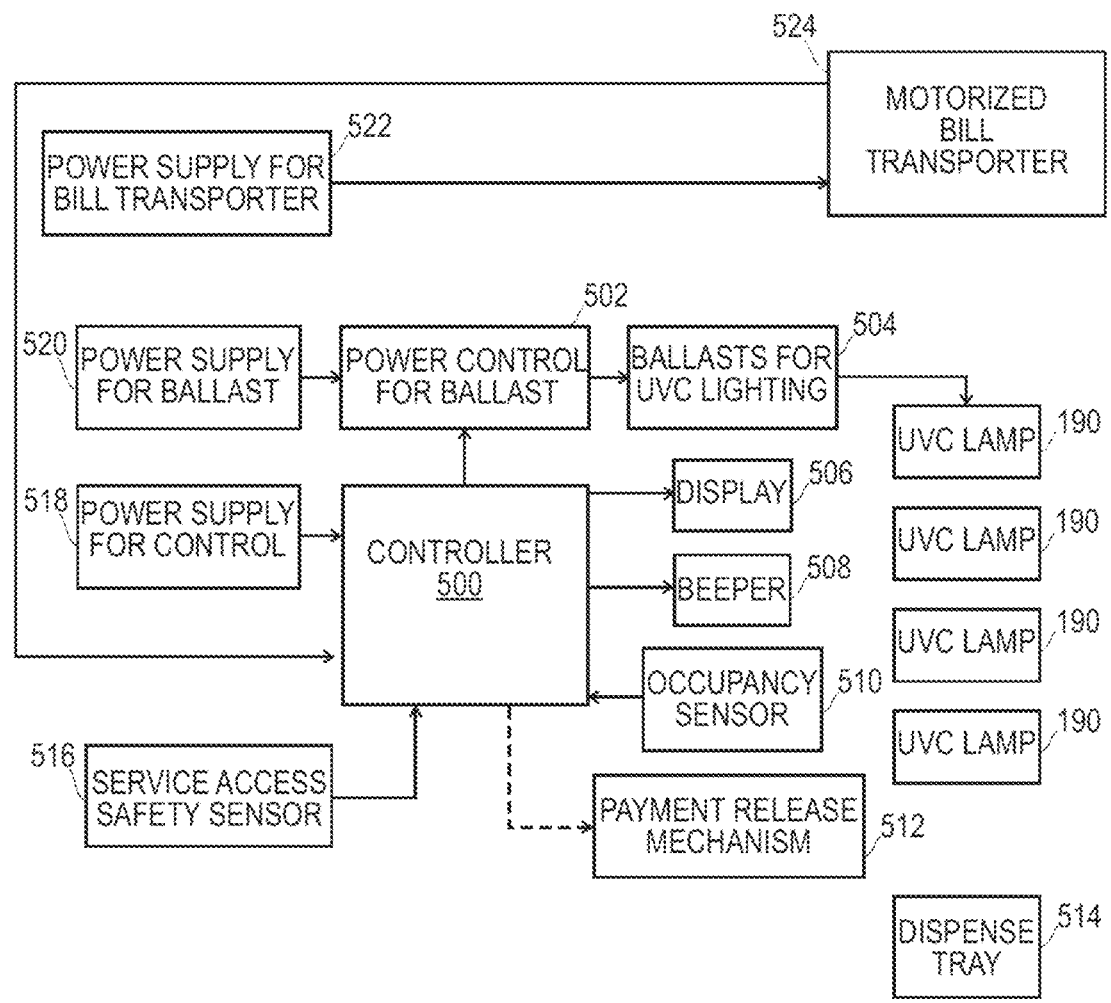
FIG. 5 illustrates a block diagram of a controller and components of the payment sanitizer system of FIG. 1.

FIG. 5 shows an embodiment of a programmed controller 500 which may suitably be utilized to control the payment sanitizer system 100. Controller 500 drives a power control module 502 for driving the ballasts 504 of the UVC lighting employed, such as the lamps 190. Controller 500 also drives a display 506, such as display 118, beeper 508 and receives inputs from an occupancy sensor or sensors 510 which detect when the area above the moveable support member 162 is occupied by a media item requiring irradiation. The sensor 510 preferably is a single reflective infrared style sensor positioned to look at a broad face of the payment media as it sits on the moveable support member 162 near the bottom of the irradiation zone. For coins, the moveable support member advantageously has a taper that compels the coin to roll towards the occupancy sensor. Other occupancy sensing arrangements might include a plurality of reflective IR sensors, transmissive IR sensors, mechanical tactile sensors, or ambient light sensors configured to detect the absence of light from the UVC illuminating sources or lamps 190 positioned on the opposing side of the payment media.

Beeper 508 is controlled to beep upon detection that an item is left on the movable support member 162 for a period exceeding a predetermined period. The predetermined period of time may be adjustable to a longer interval for extra sanitizing or a shorter interval for faster processing at the expense of anti-microbe effectiveness. Additionally, the predetermined period of time may be adjusted based on the characterized UVC light output of the bulbs corrected for time since power up or total operating hours for instance. A payment release mechanism 512 controlled by the controller 500 may be employed to prevent a customer or merchant from releasing the item to be irradiated to dispense tray 514 before irradiation is complete.

A service access safety sensor 516 may be employed to sense when service access is going on and the controller 500 powers down the UFC lamps 190 before the unit is opened to prevent dangerous exposure to a service person who needs to open the unit to service it.

A controller power supply module 518 provides the power needed by the controller 500 for its own operation. Ballast power supply module 520 provides power to the power control for ballast module 502. Transporter power supply module 522 provides the power to motorized bill transporter or bill acceptor 524.

Figure 6:
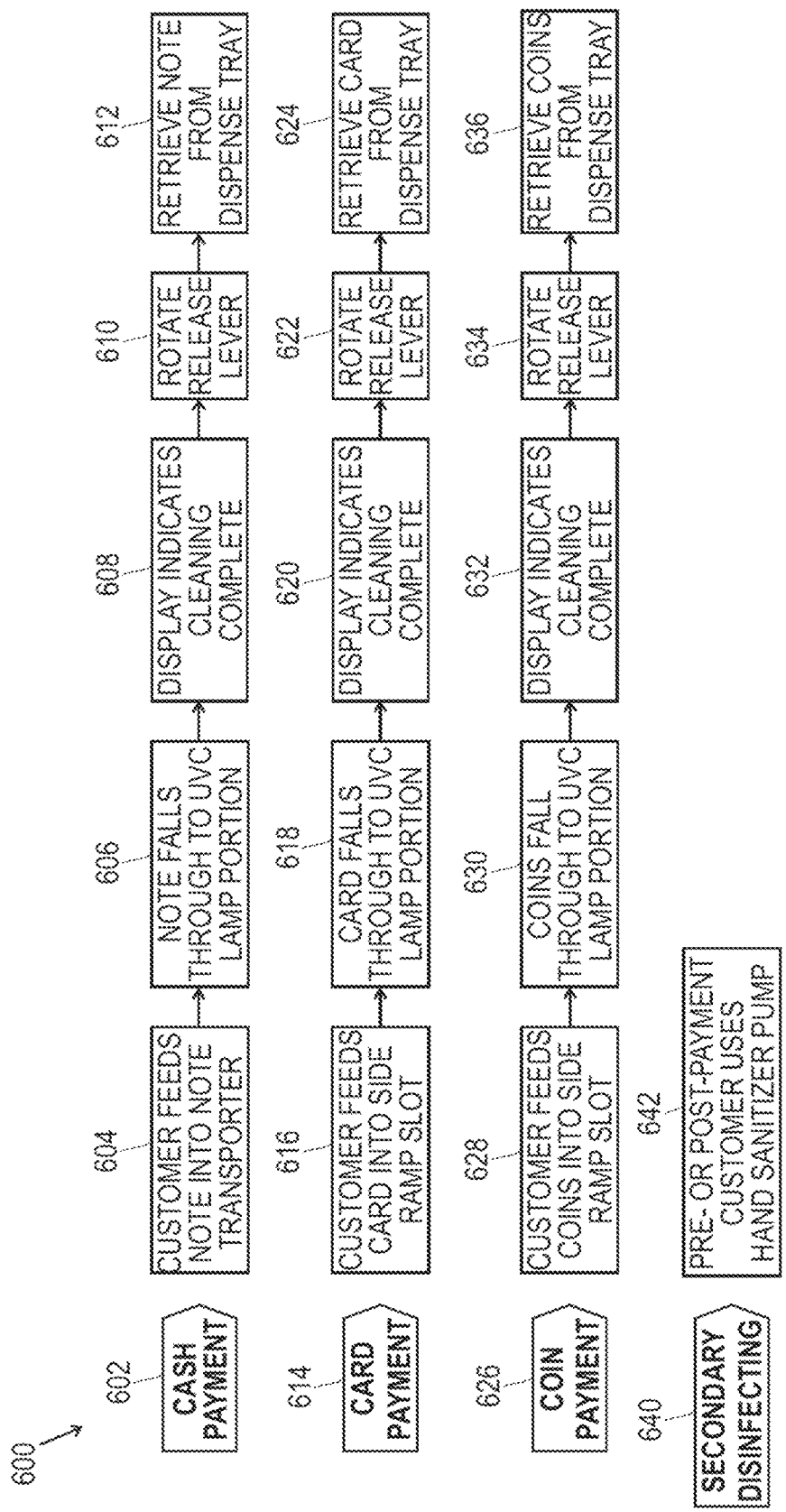
FIG. 6 shows a flowchart of a method of customer to merchant operation in accordance with the present invention.

FIG. 6 shows a method of customer payment to merchant operation 600. In steps 602-612, a cash payment process is addressed. In step 602, the customer retrieves a bill for making a cash payment. In step 604, the customer feeds the note into the note insert slot 112 of bill validator 110 which grabs the leading edge of the note and transports the note until the trailing edge of the note has passed out of the control of the bill validator 110. In step 606, the note falls under the influence of gravity until its lead edge rests on the moveable support member 162 and the note is fully in the irradiation zone 192. For American currency, the length of each note is 6.14 inches and the width is 2.61 inches and therefore the preferred length of the irradiation zone slightly exceeds 6.14 inches and the width slightly exceeds 2.61 inches. In step 608, a display, such as display 118, indicates cleaning is complete. As noted herein, a display such as display 118 may also beneficially indicate how cleaning is proceeding or how much time till completion of cleaning remains. In step 610, the merchant utilizes a release lever, such as release lever 160, allowing the note to fall under the influence of gravity to a payment retrieval tray, such as payment retrieval tray 170. In step 612, the merchant retrieves the sanitized note and adds it to the cash tray.

Steps 614-624 of FIG. 6 illustrate a card payment process. In step 614, the customer feeds a card, such as a credit or debit card to make payment. In step 616, the customer feeds the card into a side ramp slot, such as slot 140. In step, 618, the card falls into the irradiation zone 192 and comes to rest with a leading edge on the moveable support member 162. In step 620, the display 118 indicates cleaning is complete. In steps 622 and 624, the release lever is rotated and the merchant retrieves the sanitized payment card for payment processing.

Steps 626-636 of FIG. 6 illustrate a coin payment process which is similar to the credit card payment process with the exception that the process begins with the customer feeding coins into the ramp in step 628. A secondary disinfecting process may begin with a reminder step 640 followed by step 642 of the customer using hand sanitizer from a dispenser, such as sanitizer apparatus 150 either as prompted or as otherwise desired.

Figure 7:
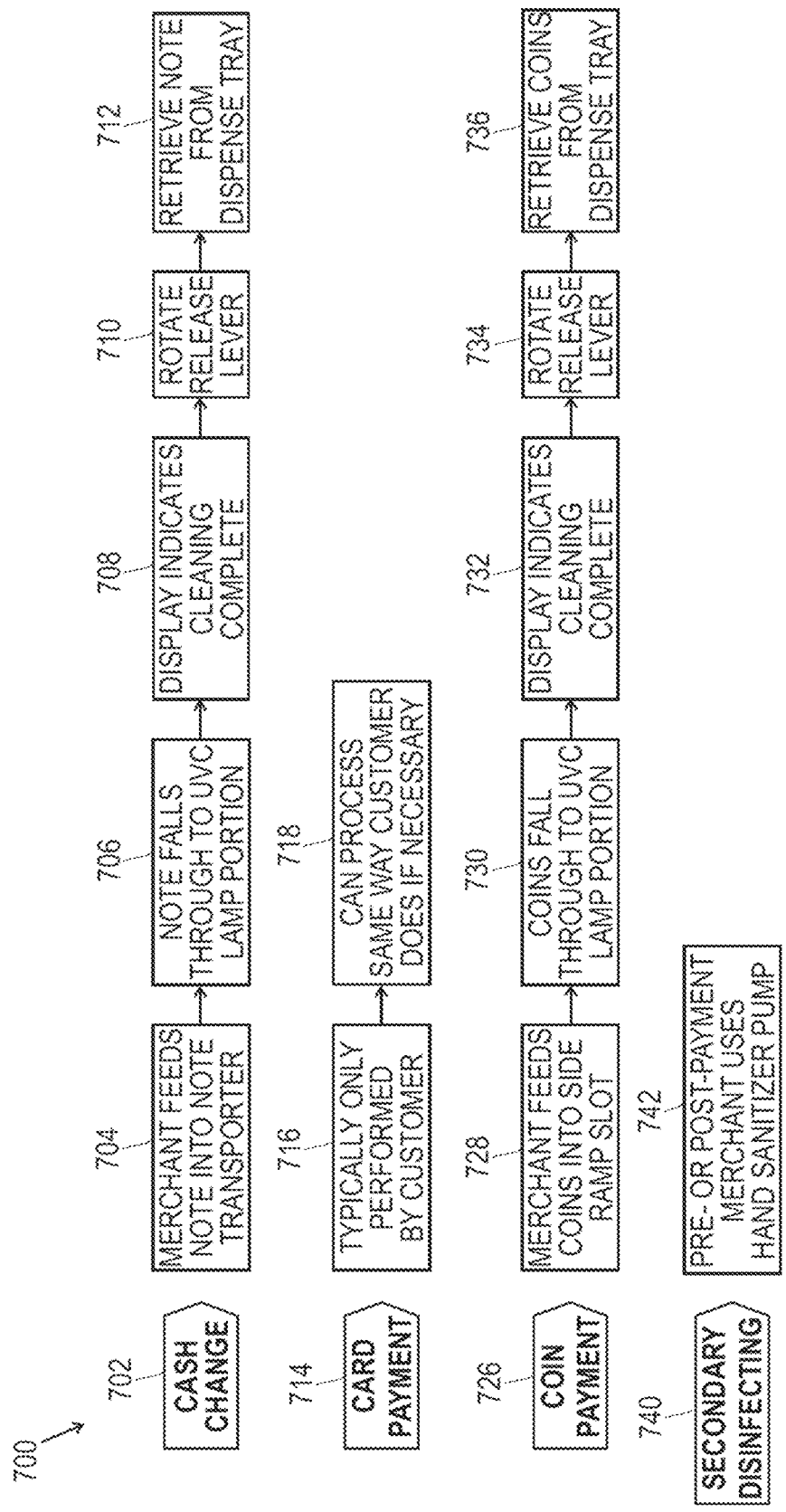
FIG. 7 shows a flowchart of a method of merchant to customer operation in accordance with the present invention.

FIG. 7 shows a method 700 of merchant to customer operation in accordance with the present invention. Steps 702-712, 714-718, 726-736 and 740-742 largely mirror the corresponding steps in FIG. 6 with the merchant doing the steps done by the customer and vice versa.

An alternate embodiment of the invention involves rotating the payment sanitizer assembly 100 ninety degrees such that it rests lower profile on the tabletop surface. This embodiment requires the use of a motorized bill transport path 112 to thrust the note into the irradiation zone with minimal help from gravity. Drag resistance of the note standing on its short edge is very small making note propulsion possible with minimal risk of jamming.

In an alternate embodiment shown in FIG. 8, a payment sanitizer system 800 has a payment media passageway better adapted for banknote and credit cards, but less favorable for coin travel for reasons discussed below. In this embodiment, a payment card entrance slot 840 is located on the top of the apparatus and follows a substantially straight downward path towards an irradiation zone 892 (FIG. 9). This embodiment also features a visual indicator light bar 810 to inform the customer that payment media sanitizing is taking place. Preferably, the portion of the light bar 810 which is lit is representative of the approximate size of the payment media—long for a banknote and short for a credit card. The location of the lit portion of the light bar approximates where the payment media is situated as it falls into the irradiation zone 892, dwells on moveable support member 862 (FIG. 9), and then is released into dispense tray 870. Hand sanitizer can be applied by the customer or the merchant using hand sanitizer 850.

Figure 8:
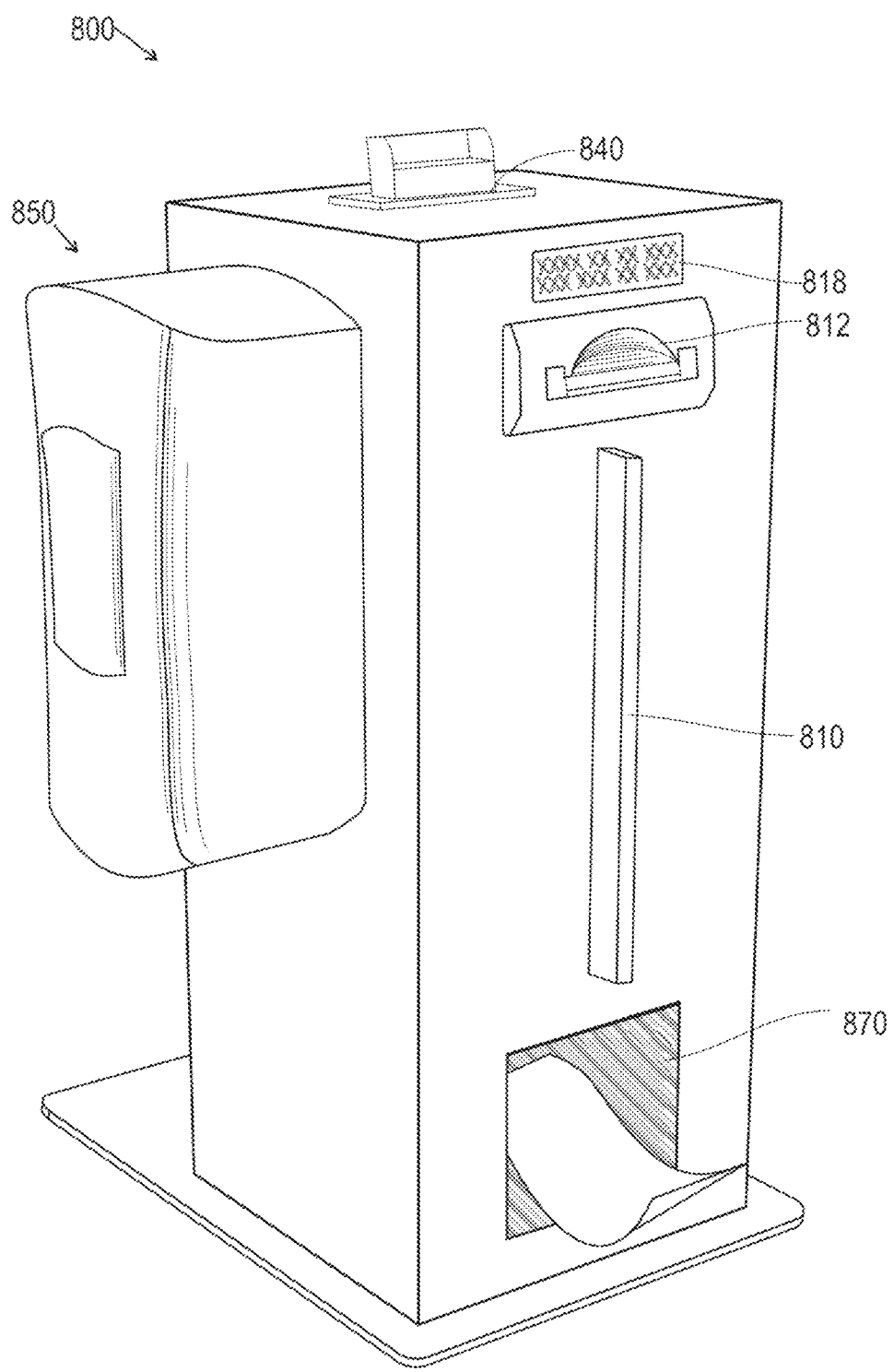
FIG. 8 shows an alternate embodiment of the payment sanitizer system for banknote and plastic card sanitizing.
Figure 9:
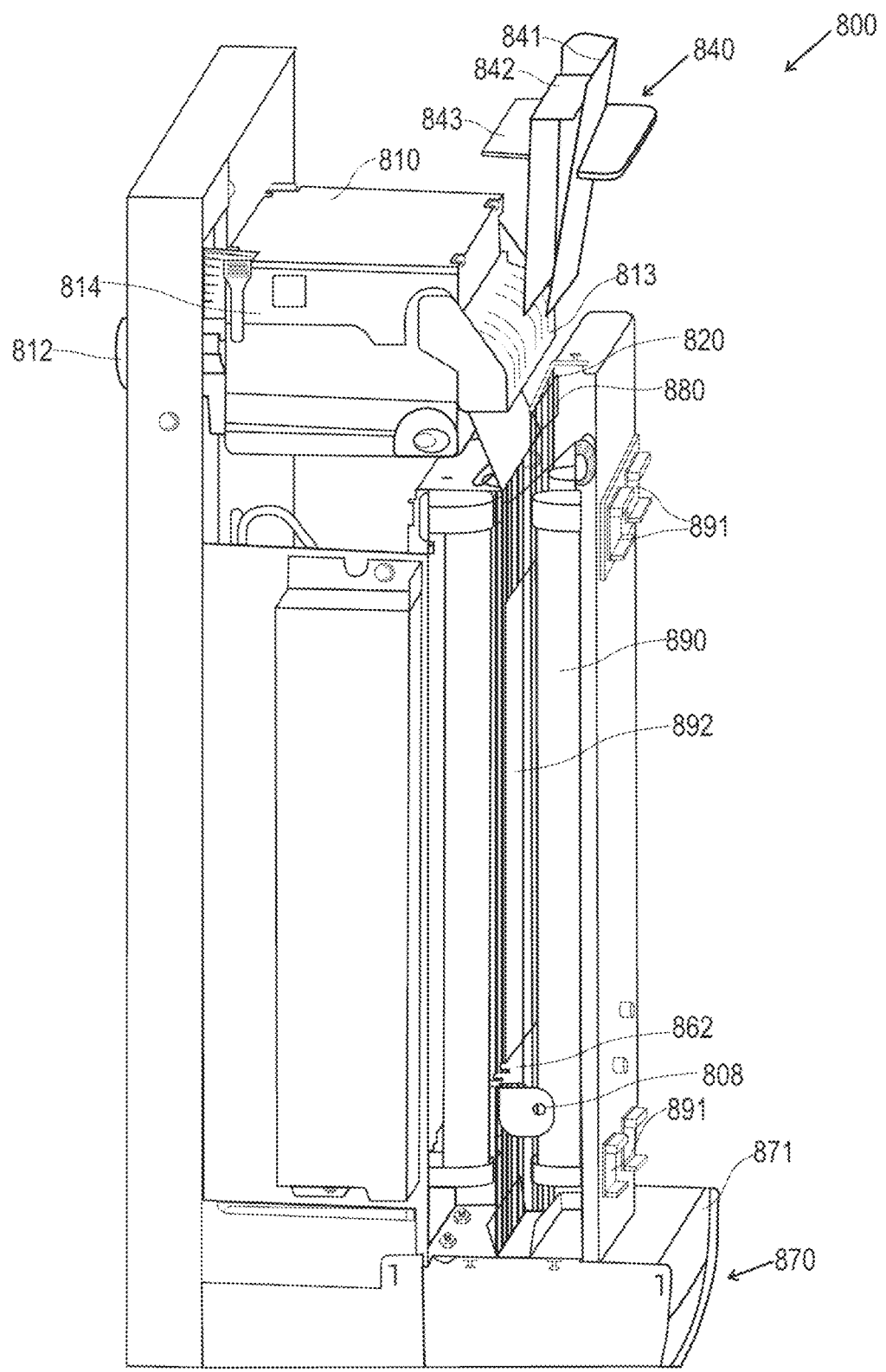
FIG. 9 shows an interior right-side view of the alternate embodiment of FIG. 8 with a cutaway view of the UVC irradiation zone.

FIG. 9 provides a cutaway view of the sanitizer apparatus 800 illustrating a media passageway which accommodates banknotes fed into validator 810 and payment cards (credit, debit, store cards, and the like) through card entrance slot 840 (FIG. 8). The processing for banknotes starts by a customer feeding the note into bill insert slot 812. The note is transported forward by validator transport 814 and deflected downward by deflector 813. Preferably, validator 810 only advances the bill to a point at which it releases it, if it first determines the bill is substantially flat and therefore free of folds that might compromise cleaning ability of the UVC irradiation to directly reach 100% of the note's surface. Otherwise, the validator 810 returns the note to the customer and display 818 prompts the customer to flatten the note and try again. Lower ramp 820 directs the lead edge of the note and ensures the note falls into the space spanned by the two halves of the irradiation chamber comprised of four UVC bulbs collectively 890 arranged as addressed above with two on one side of the note or other payment media and two on the other side held by bulb sockets collectively 891. The banknote is constricted into a zone between the bulbs by way of several vertically hung wires collectively 880. Preferably, the wires are spaced 0.5" apart and made of 0.01" diameter stainless steel. Each half of the chamber may use a single wire that is pulled tight around mounting studs at the top and bottom of the chamber to achieve the 0.5" spaced vertical wire runs across the width of the chamber. This wire guided pathway in this embodiment is ideal for bank notes and plastic cards but is problematic for coins as they could fall between the wire spacings. The spacing described strikes a good balance of maintaining control of banknotes and cards without blocking too much of the sanitizing irradiation.

An advantage of vertical wire runs 880 as a media pathway is that they provide a very low friction surface for banknotes which are lightweight and pliable. Any substantial friction in the media pathway will inhibit the ability of the banknote to freefall all the way down to movable support member 862. Additionally, using vertically oriented wires prevents any banknote defects such as a dog-eared corner or a slight crease from getting caught within the track. Once the banknote hits movable support member 862, it is optimally positioned to receive UVC light from the surrounding bulbs 890.

Figure 10:
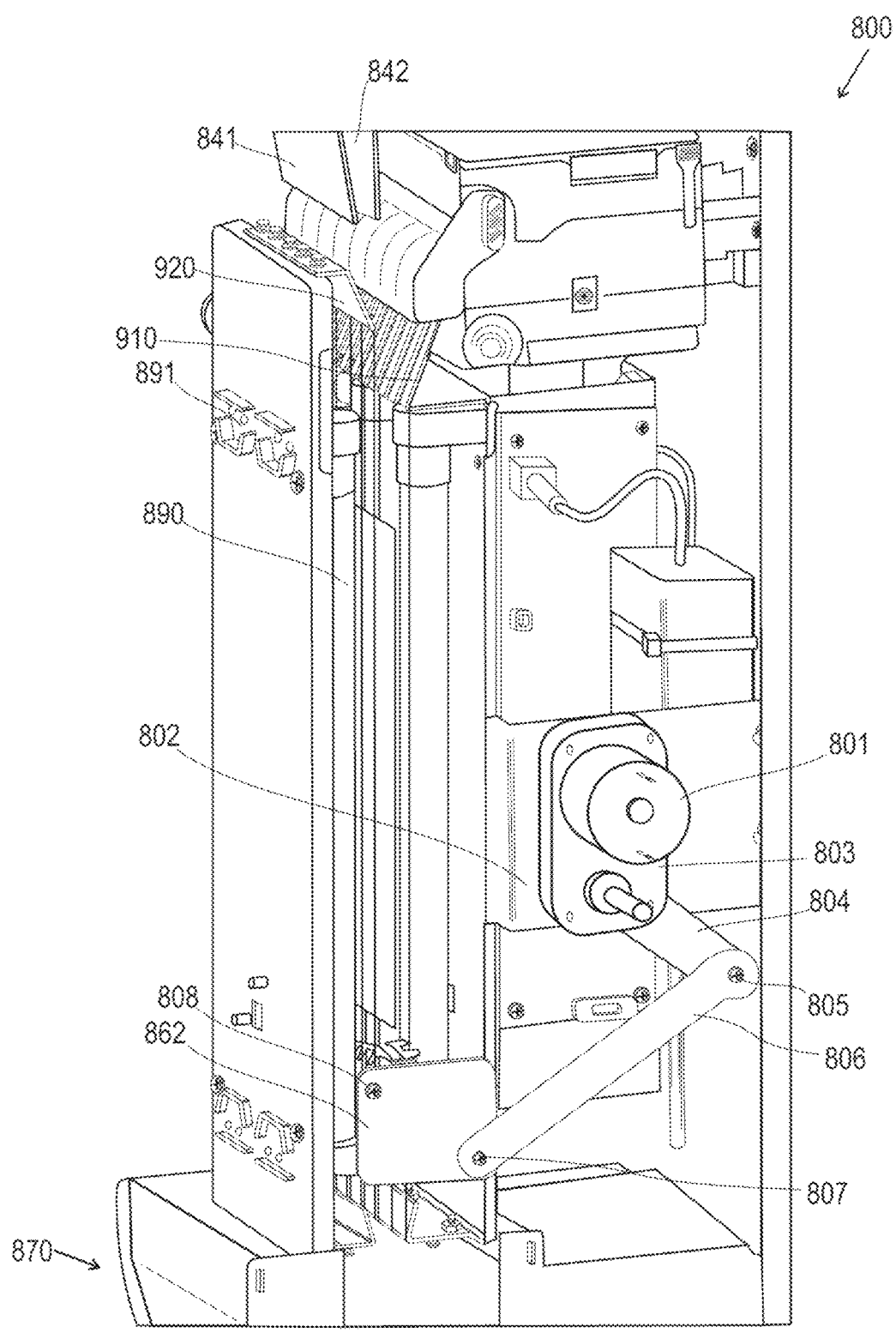
FIG. 10 shows an interior left-side view of the alternate embodiment of FIG. 8 with a cutaway view of the UVC irradiation zone.
Figure 11:
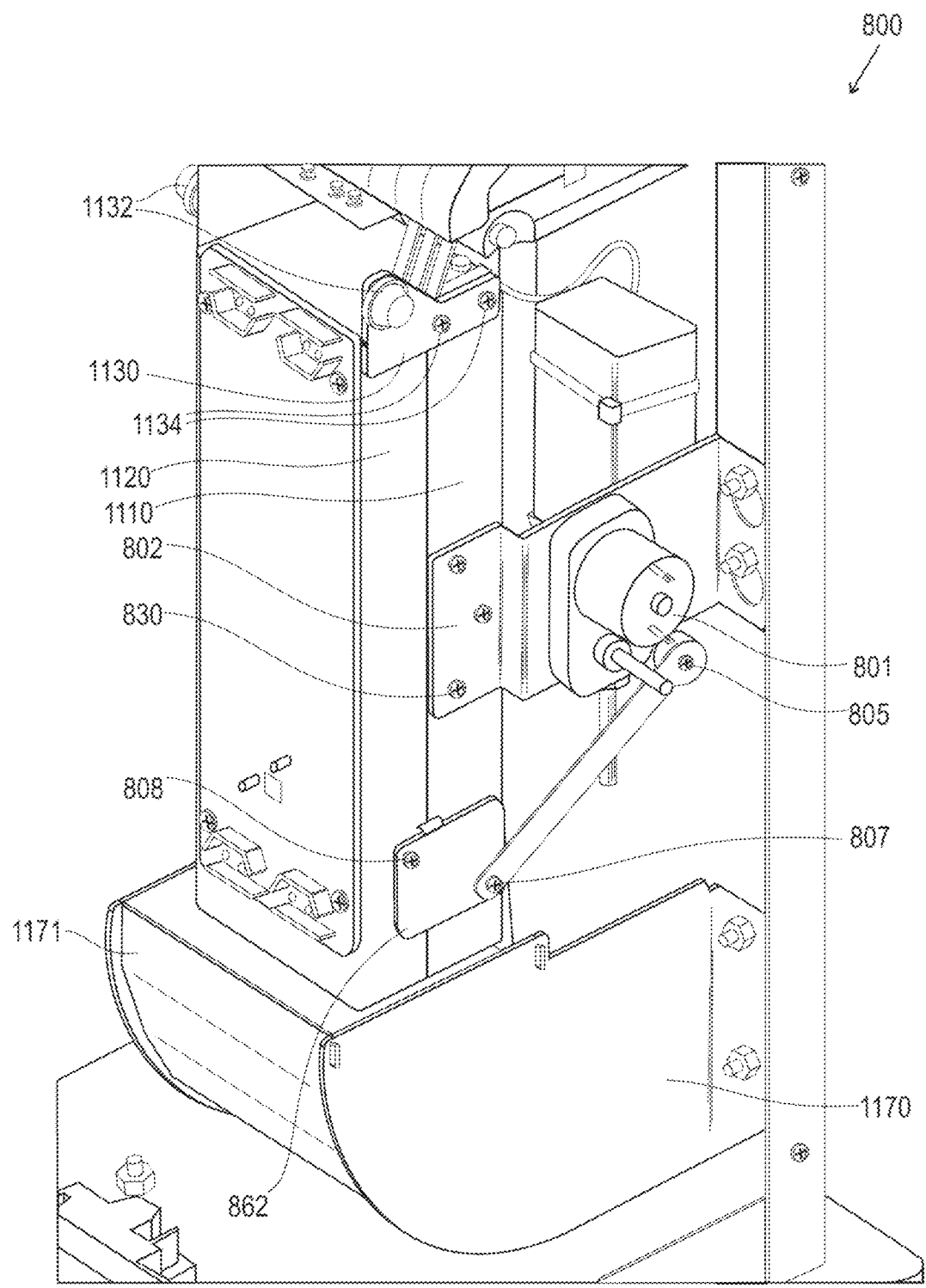
FIG. 11 shows the interior left-side view of the alternate embodiment of FIG. 8 with the outer cover removed and with the mechanism in the fully closed position with the movable support member horizontal.

The other side of the chamber of sanitizer apparatus 800 is illustrated in the cutaway views of FIG. 9 and FIG. 10. In these views, the operation of moveable support member 862 is better shown. Moveable support member 862 acts a platform for the payment media to sit on top of while supported between wires 880 and exposed to the UVC radiation. It has protruding fingers that extend between the media guide wires to ensure there is no chance of the banknote slipping between the wires and movable support member while the movable support member is in its horizontal orientation shown in FIG. 10. Moveable support member 862 is secured to both ends of the rear chamber half 1120 (FIG. 11) with a pivoting connection 808 (FIGS. 9 and 10). The movable support member is operable to rotate to a vertical position (FIG. 13) when the irradiation time is complete. An articulating drive shaft formed by elements 804 and 806 connected together with hinges 805 and 807, respectively, and connected to the shaft of gear motor 801 rotate moveable support member 862 vertical when the motor 801 is energized to turn clockwise. The motor is mounted to motor mounting plate 802 which is attached rigidly to a front wall of the apparatus. Mounting plate 802 also rigidly connects to the front half of irradiation chamber 1110 (FIGS. 11 and 12) with screws 830 (FIG. 11). Once rotated vertical by the motor, moveable support member 862 is no longer blocking the payment media (FIGS. 12 and 13), and that media is free to fall to retrieval tray 870 (FIG. 8) for customer retrieval.

Figure 12:
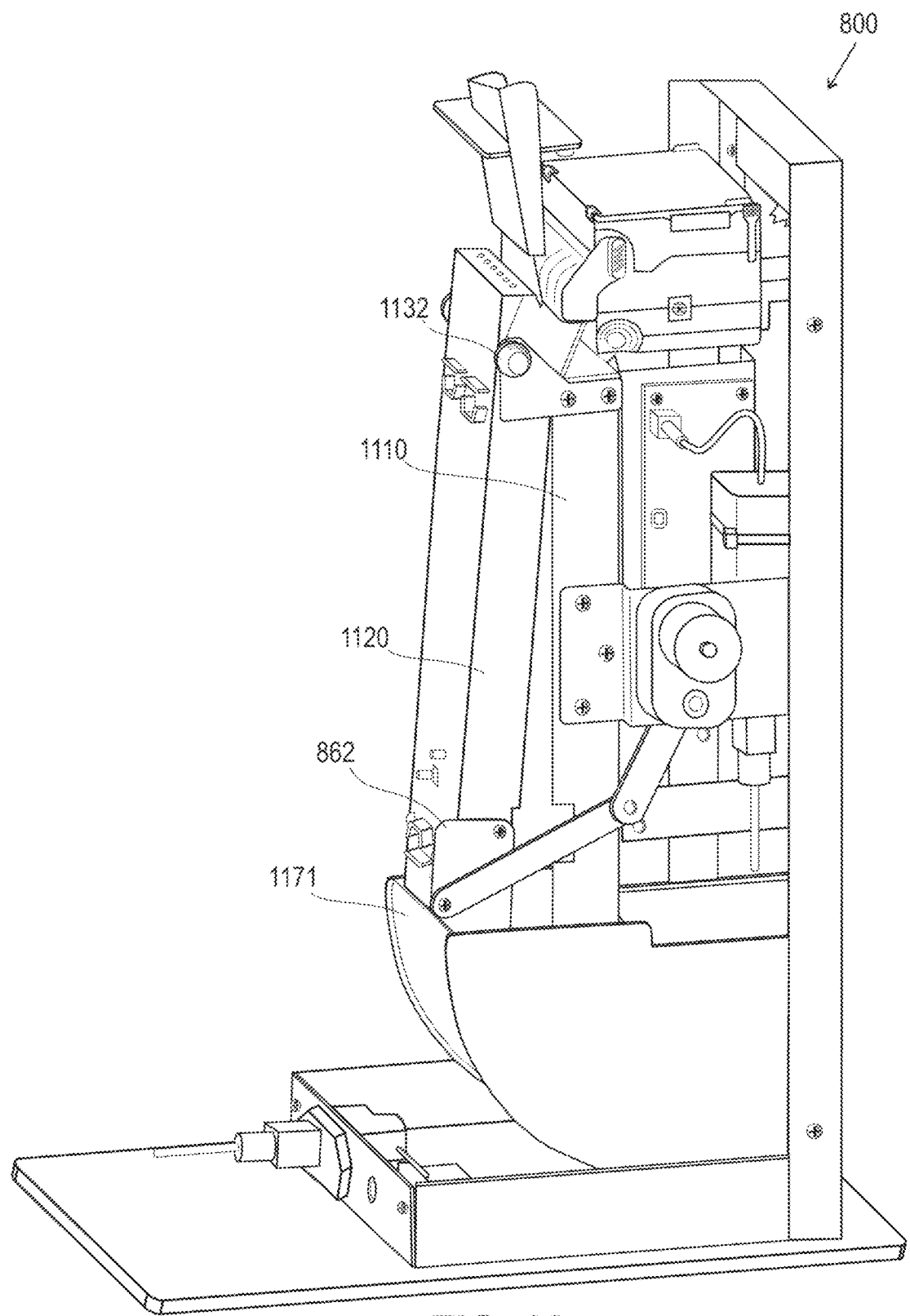
FIG. 12 shows the interior left-side view of the alternate embodiment of FIG. 8 with the outer cover removed and with the mechanism in the fully opened position with the movable support member vertical.
Figure 13:
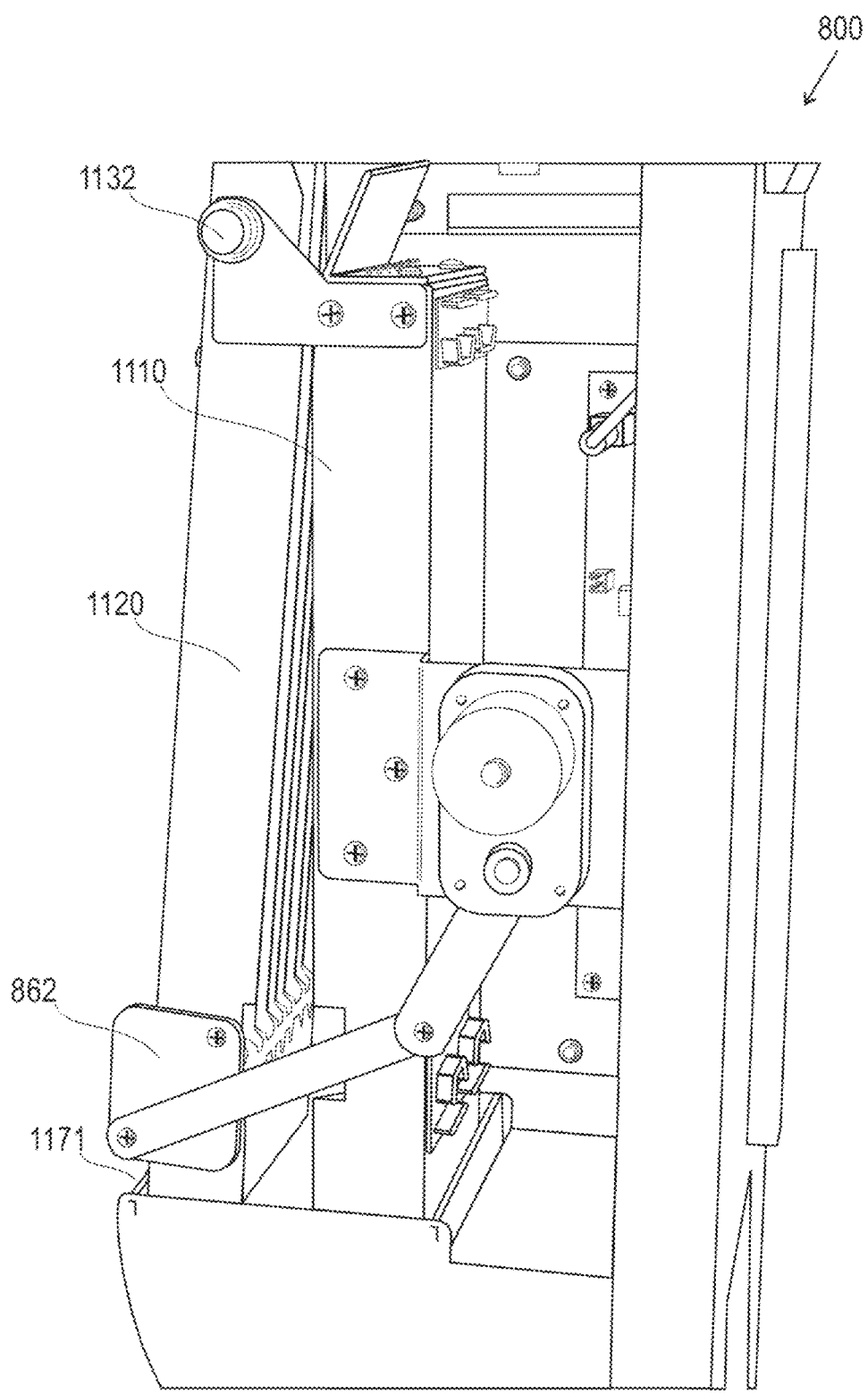
FIG. 13 shows an alternate angle of the state of the apparatus from FIG. 12 to add clarity to the movable support member mechanism.

After moveable support member 862 is rotated vertically, continued clockwise motion of the motor shaft acts to pivot the rear irradiation chamber 1120 away from the front half of the chamber 1110 about pivoting hinge 1132 (FIG. 11). The rear chamber is supported at the top of the apparatus by bracket 1130 that is rigidly affixed to the front chamber 1120 with screws 1134 (FIG. 11). The rear chamber continues to pivot away from the front chamber until the rear chamber is stopped by the dispense tray backstop feature 1171 as seen in FIGS. 12 and 13.

A controller 1600 (FIG. 16) is configured to sense the backstop position by way of an end position detector 1410 (FIG. 14) to turn off the motor 801 (FIG. 10). The end position detector may be a limit switch, reed switch, angular position encoder, or may detect an increase of motor current associated with a stall condition of hitting the backstop as a way to detect when the rear chamber has reached the end of travel. It will also be noted that the motor could be driven for a fixed period of time to turn the movable support member vertical and spread the chambers apart based on an open loop system characterization. The pivoting motion of the rear chamber with respect to the front chamber during payment dispensing further assists in coaxing a banknote to release from the chamber and fall into the displace tray when the irradiation is complete, even if it has folds that would otherwise cause the note to cling to the side walls.

Figure 14:
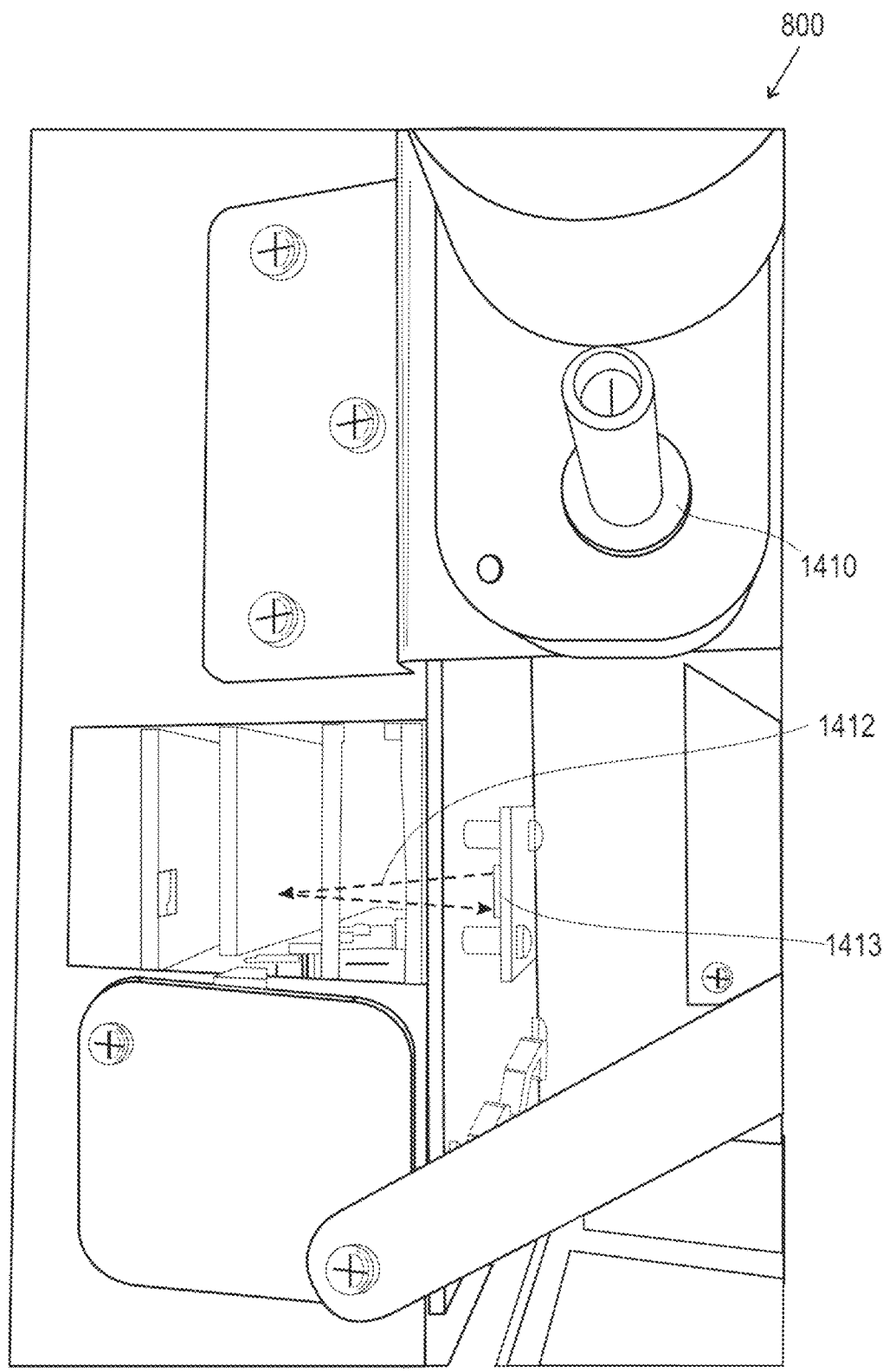
FIG. 14 shows a cutaway view highlighting the behavior of the payment media sensor located above the movable support member.

The passage of the payment media from the chamber into the dispense tray is confirmed by seeing the absence of media using the movable support member media sensor 1613, such as sensor 1413 of FIG. 14. At that point in time, controller 1600 drives the motor counterclockwise to return the movable support member back to the horizontal position. Once fully horizonal and front and rear chambers have pivoted closed again, the side walls of each chamber touch preventing further rotation of the motor 801 (FIG. 11). The motor end position detector 1410 (FIG. 14) can again be used to determine the fully closed end position as described with the fully open end position above.

Returning back to FIG. 9, when a card is presented into the sanitizing apparatus 800, the customer places the card against the rear wall 841 of the card entrance slot 840. The entrance slot is mounted to the top of the apparatus 800 (FIG. 8) with a mounting flange 843. A front wall 842 is used to both constrain the motion of the card within the entrance path and to baffle the UVC light from escaping the top of the enclosure. Once the card is released into the slot, it falls along back wall 841 until it lands between the note deflector 813 and ramp 820 of the rear chamber. The card will continue to fall under gravity until it lands on the movable support member 862 and is detected electronically by sensor 1613 positioned to detect objects sitting on the movable support member. The controller, upon detecting an object on the movable support member that did not come with a corresponding signal from the validator 810, will conclude the object is a card and send a signal to display 818 that card sanitizing is in progress.

As a safety feature, a lock out switch 1516 ensures system power is cut and the UVC lamps are off when a service person opens the sanitizer apparatus 800 for service to clear a jam, or the like.

Figure 15:
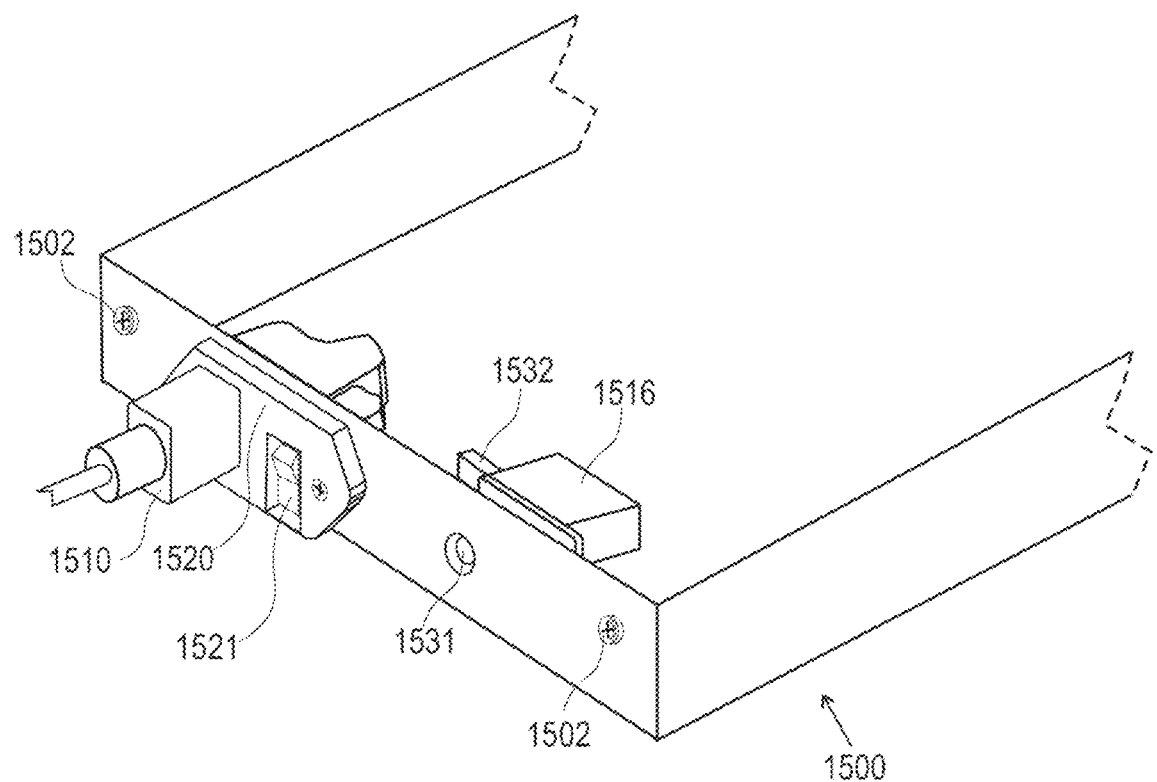
FIG. 15 shows a cutaway perspective view of the base and safety cutout switch of the alternative embodiment of FIG. 8.

FIG. 15 illustrates a cutaway perspective view of the base of the sanitizer system 800 for ease of illustration of the input power system of this embodiment. An AC power cord 1510 provides input power to the apparatus when connected into IEC connector 1520. Power switch 1521 is available for users to cycle power on and off to the system. A safety lockout sensor 1516 is mounted to bracket 1532 which fastens the switch to an outer enclosure (not shown) of the apparatus 800. Preferably lockout sensor 1516 is a line voltage rated switch that passes current across its terminals when its plunger 1531 is depressed. The outer enclosure is screwed to the base 1500 with screws 1502. When fully fastened, the outer enclosure presses against plunger 1531 and switch 1516 passes current from the IEC connector through to the controller 1600. If the outer enclosure is removed, the plunger is no longer depressed and the power is cut from system.

Figure 16:
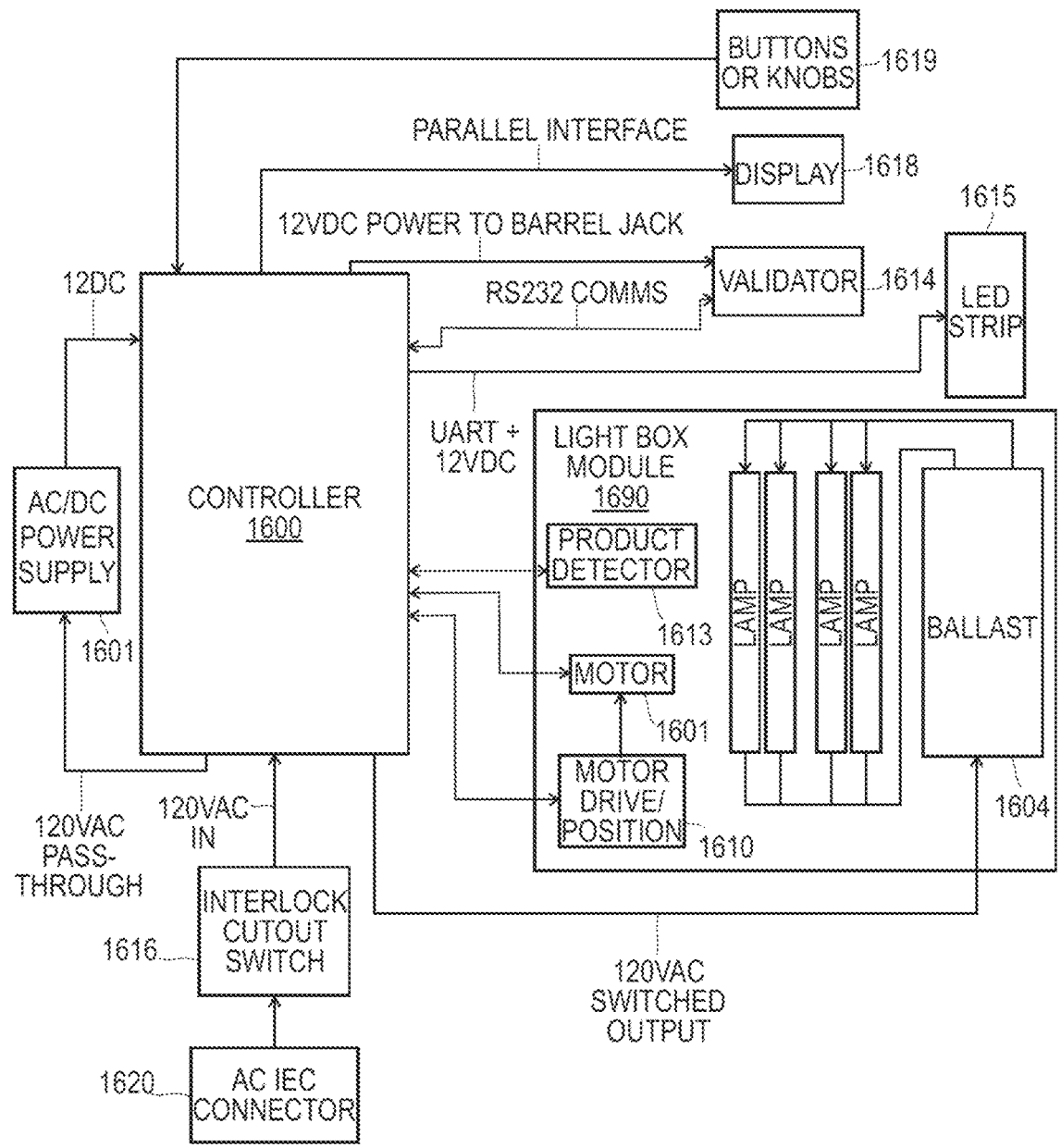
FIG. 16 shows a block diagram of a controller and components of the alternate embodiment of FIG. 8.

FIG. 16 shows a block diagram of a programmed controller 1600 for the system 800. Input power 1620 flows through safety interlock switch 1616 to the controller 1600. The controller, passes the AC input power over to an AC to DC power supply 1601 to generate 12 VDC used for driving a bill validator 1614, such as bill validator 810 and its associated motorized transport path. The 12 VDC is further regulated down to 3.3 VDC for the controller's circuitry inclusive of a processor and interface logic to the various peripherals. The controller energizes a relay to pass line voltage out to the UVC lamp ballast 1604 when the chamber needs to be energized.

On the low voltage control side, controller interfaces with a moveable support member motor 1601, a moveable support member motor detector 1610 and product detector 1613. The product detector 1613 is configured to detect payment media located just above the movable support member 862 in the irradiation chamber. Product detector 1613 is preferably a reflective IR type sensor that is mounted to the front of irradiation chamber 1110 and peers through a small opening positioned between the UVC lamps. An infrared ray 1412 emitted from the sensor board passes between the tubes and reflects off the payment media located on the movable support member and back to the sensor 1413.

Controller 1600 also interfaces with a validator 1614 over a serial communication link for the purpose of determining a banknote has been presented and has been passed by the transport path, as well as, determining denomination information. Instructions to the users are sent by the controller out to a display 1618. Feedback from users is monitored in the form of buttons and knobs 1619 that may be present for controlling UVC irradiation time, for instance. The controller also drives an LED strip display 1615, such as display 810 to indicate progress of the UVC irradiation cycle.

To ensure the proper performance of the irradiation chamber there are a series of inks that change color for purposes of indicating disinfection has been successful. In one embodiment of the present invention, a test card or strip shaped like a bill with such ink may be advantageously employed as a test of unit effectiveness upon set up at the start of the business day, for example.

The target UVC irradiance is nominally 15 mJ/cm^2 across the surface which takes approximately 2-3 seconds of time in the chamber. This dosage level will substantially reduce the presence of many types of viruses and bacteria by 90% to 99%. A knob or series of buttons, can be used to adjust the UVC dosage up or down whereby the controller 1600 interprets the action to increase dosage by increasing dwell time of the media located on the movable support member 862 prior to ejecting the media to the dispense tray or prompting an audio cue for the user to manually eject the media, or correspondingly, to reduce the dosage by reducing the dwell time of the media on the movable support member.

While the present invention has been primarily disclosed in the context of a practical, small, lightweight and relatively inexpensive approach, it will be recognized that additional features may be added thereto. As one example, in addition to UVC, another germicidal approach, such as a spray and brush system may be added. While UVC fluorescent lamps are currently preferred, it will be recognized that UVC LEDs are available and with time will be expected to come down in cost so they or some other source might be employed in the future. Additionally, the present application refers to currency, bills, banknotes and notes interchangeably. While the disclosure is made with respect to U.S. currency and its dimensions, it will be recognized that dimensions may be adapted to suit other currency systems as needed.

We claim:
1. Payment media sanitizing apparatus comprising:
  a thin payment media directing mechanism that directs the thin payment media from an insertion point to a sanitization zone internal to the payment sanitizing apparatus;
  the sanitization zone having a length slightly longer than a longest thin payment media to be sanitized by the payment media sanitizing apparatus and comprising a thin payment media support and associated ultraviolet sources irradiating the thin payment media when the thin payment media is in the sanitization zone;

and a release mechanism comprising a movable support member supporting a leading edge of the thin payment media when the thin payment media is in the sanitization zone during sanitizing and a mechanical release lever operated to return the thin payment media to a return retrieval tray.

2. The payment sanitizing apparatus of claim 1 wherein the thin payment media comprise at least one of bills, coins, credit cards, checks or coupons.

3. The payment sanitizing apparatus of claim 1 wherein the directing mechanism comprises a motorized bill transport.

4. The payment sanitizing apparatus of claim 3 wherein the motorized bill transport is part of a bill validator which ensures that a thin payment media comprising a note is flat when its leading edge reaches the sanitization zone.

5. The payment sanitizing apparatus of claim 1 wherein the input transport mechanism comprises a chute sized to gravity feed a coin or credit card.

6. The payment sanitizing apparatus of claim 1 wherein the closely spaced thin payment media support comprises at least a portion defined by perforated aluminum or quartz.

7. The payment sanitizing apparatus of claim 1 wherein the ultraviolet sources comprise ultraviolet lamps emitting radiation in the UVC band and spaced no more than one inch apart, and between which the payment media passes.

8. The payment sanitizing apparatus of claim 1 further comprising:
   a sensor to detect the thin payment media is fully in the sanitization zone;
   a controller to determine how long the thin payment media has been irradiated; and
   a display controlled by the controller to indicate the thin payment media has been sanitized after a predetermined period of irradiation has occurred.

9. The payment sanitizing apparatus of claim 1 wherein the thin payment media support comprises at least a portion formed by small spaced wires.

10. The payment sanitizing apparatus of claim 9 wherein:
   the moveable support member is controllably rotatable by a motor to move the closely spaced thin payment media support apart facilitating the thin payment media falling under the influence of gravity to the retrieval tray.

11. The payment sanitizing apparatus of claim 1 wherein the sanitization zone is at least 6.25 inches long and 2.65 inches wide.

12. The payment sanitizing apparatus of claim 1 having overall dimensions of approximately 17 inches tall, 8 inches wide, and 10 inches deep or less.

13. The payment sanitizing apparatus of claim 1 further comprising:
   a display to indicate an extent of completion of sanitizing on an ongoing basis.

14. The payment sanitizing apparatus of claim 1 having a lockout switch to prevent opening the apparatus when the associated ultraviolet sources are on.

15. The payment sanitizing apparatus of claim 7 wherein the mechanical release lever is not operable until sanitizing is completed.

16. The payment sanitizing apparatus of claim 1 further comprising a note shaped test card with special ink indicating a completion status of sanitizing utilized to adjust a duration of sanitizing to reflect a current efficiency of said ultraviolet sources.

17. The payment sanitizing apparatus of claim 4 wherein the bill validator determines a denomination of a banknote transported through the bill validator.

18. The payment sanitizing apparatus of claim 1 wherein the thin payment media support comprises two closely spaced supports, one arranged on either side of the sanitization zone.

19. The payment sanitizing apparatus of claim 1 wherein the associated ultraviolet sources comprise UVC LEDS.

20. The payment sanitizing apparatus of claim 1 wherein the moveable support member supports a leading edge of the thin payment media in a first position and allows the thin payment media to pass to the retrieval tray when the moveable support member is moved to a second position.

* * * * *